US005565493A

United States Patent [19]

Nakata et al.

[11] Patent Number: 5,565,493

[45] **Date of Patent: *Oct. 15, 1996**

[54] COLLAGEN METABOLISM AMELIORANT AND ITS USE IN THE STIMULATION OF HAIR GROWTH

[75] Inventors: Masanori Nakata; Shintaro Inoue; Mikio Sotomura, all of Odawara; Junsei Taira, Hadano; Itaru Miyamoto, Chigasaki, all of Japan

[73] Assignee: Kanebo, Ltd., Tokyo, Japan

[ * ] Notice: The term of this patent shall not extend beyond the expiration date of Pat. No. 5,332,758.

[21] Appl. No.: 229,724

[22] Filed: Apr. 19, 1994

Related U.S. Application Data

[60] Division of Ser. No. 4,107, Jan. 13, 1993, Pat. No. 5,332,758, which is a continuation-in-part of Ser. No. 838,706, filed as PCT/JP91/00937, Jul. 12, 1991, abandoned.

[30] Foreign Application Priority Data

| | | | |
|---|---|---|---|
| Jul. 13, 1990 | [JP] | Japan | 2-186762 |
| Jul. 13, 1990 | [JP] | Japan | 2-186763 |
| Jul. 12, 1991 | [WO] | WIPO | PCT/JP91/00937 |

[51] Int. Cl.$^{6}$ .................... A61K 31/195

[52] U.S. Cl. .................... 514/561

[58] Field of Search .................... 514/561

[56] References Cited

U.S. PATENT DOCUMENTS 4,874,791 10/1989 Adachi et al. .................... 514/558

5,332,758 7/1994 Nakata et al. .................... 514/561

OTHER PUBLICATIONS

Ebata et al, *Chemical Abstracts,* vol. 67, No. 5, abstract no. 22129j, 1967.

Eloff et al, Chemical Abstracts, vol. 72, No. 5, abstract no. 19099x, 1970.

Filippova, *Chemical Abstracts,* vol. 92, No. 15, abstract no. 214623z, 1980.

Reading et al., *Chemical Abstracts,* vol. 110, No. 20, abstract #180411f, 1989, p. 486.

Naoi et al., *Chemical Abstracts,* vol. 111, No. 15, abstract #131217j, 1989, p. 486.

*Primary Examiner*—Marianne M. Cintins
*Assistant Examiner*—William R. A. Jarvis
*Attorney, Agent, or Firm*—Flynn, Thiel, Boutel & Tanis, P.C.

[57] ABSTRACT

This invention relates to a collagen metabolism ameliorant containing N-methyl-L-serine as an active ingredient, more particularly, a collagen metabolism ameliorant efficacious against collagen hypometabolism caused by aging or diseases accompanied with an abnormal cumulation of collagen, such as hepatic and pulmonary fibroses, keloid, hypertrophic scar, scleroderma, fibrosis in the scalp, or the like. Furthermore, the invention includes a hair growth stimulant containing this collagen metabolism ameliorant.

5 Claims, No Drawings

COLLAGEN METABOLISM AMELIORANT AND ITS USE IN THE STIMULATION OF HAIR GROWTH

This is a division of U.S. Ser. No. 08/004,107, filed Jan. 13, 1993, now U.S. Pat. No. 5,332,758, which is a continuation-in-part of U.S. Ser. No. 07/838,706, filed as PCT/JP91/00937, Jul. 12, 1991 abandoned.

TECHNICAL FIELD

The present invention relates to a collagen metabolism ameliorant containing N-methyl-L-serine (hereinafter referred to as "MSE") as an active ingredient, more particularly, a collagen metabolism ameliorant efficacious against collagen hypometabolism caused by aging or diseases accompanied with an abnormal accumulation of collagen, such as hepatic and pulmonary fibroses, keloid, hypertrophic scar, scleroderma, fibrosis in the scalp, or the like.

Furthermore, this invention relates to hair growth stimulants and skin aging inhibitors containing such a collagen metabolism ameliorant.

The term "collagen metabolism amelioration" herein referred to is meant by normalization of a condition such that synthesis of collagen has abnormally progressed due to the loss of balance between synthesis and decomposition of collagen, or reactivation of such a condition as collagen hypometabolism. Further, the term "collagen metabolism" is meant by a phenomenon such that collagen is being renewed at a constant rate as the collagen is undergoing synthesis and decomposition, namely, a metabolic turnover.

BACKGROUND ART

It has so far been suggested that in diseases accompanied with an abnormal accumulation of collagen (hepatic and pulmonary fibroses, keloid, hypertrophic scar, scleroderma, fibrosis in the scalp, or the like), synthesis and decomposition of collagen have been unbalanced.

For example, hepatic fibrosis accompanied with hepatic cirrhosis arises from an increase of collagen biosynthesis [Science, Vol. 176, P. 795, (1972)] or a decrease of collagenolytic activity [Biochemical Journal, Vol. 118, p. 229 (1970) and Life Sciences, Vol. 30, p. 1379, (1982)].

Alternatively, it has been known that in the scalp of androgenic alopecia, synthesis and decomposition of collagen are unbalanced, resulting in an abnormal accumulation of collagen, whereby fibrosis of the scalp is promoted [Hair Research, p. 244 (1981), edited by Orfanos, Montagna, Stuttgen, Springer-Verlag Berlin Heidelberg]. In consequence, it is assumed that tensing and a decrease of blood circulation of the scalp, deactivation of hair matrix cells or the like occurs to induce alopecia.

The decrease of the collagenolytic activity has been assumed to be caused by a decreased collagenase activity in each organ and/or skin fibroblasts [Journal of Clinical Investigation, Vol. 56, p. 1175 (1975)], so that an enhancement of a collagenase activity has been desired. This has been pointed out in medical treatments of, for example, hepatic cirrhosis.

Alternatively, metabolism of skin collagen is decreased not only by diseases as mentioned above but also by aging, whereby the collagen remains in the body for a long time and is subjected to a chemical modification to promote crosslinking thereof. It has been known that there is formed a vicious circle such that the collagen thus loses its function as an anchorage for cells with the consequence that collagen metabolism is further decreased. Accordingly, it has been said that aging of skin may be prevented by restraining the decrease in the collagen metabolism as well as preventing the formation of crosslinkages in collagen.

In order to sever such a vicious circle of the decrease in the collagen metabolism, it is required for collagen not to stay long in the body. For this purpose, an enhancement of the collagenase activity has been strongly desired.

The collagenase is a rate limiting enzyme acting during decomposing interstitial collagens (type-I, type-II and type-III collagens) in connective tissues, which plays an important role in collagen metabolism.

The collagenase is produced as a precursor, i.e., procollagenase that is secreted from cells and assumed to be activated in vivo by a protease such as plasmin, stromelysin or the like [Biochemical Journal, Vol. 166, p. 21 (1977) and Proceedings of the National Academy of Sciences of the U.S.A., Vol. 86, p. 2632 (1989)].

From the above, a substance to promote the production of the procollagenase, namely, a collagen metabolism ameliorant, is considered to be efficacious, in medical treatment, against diseases accompanied with an abnormal accumulation of collagen or, in amelioration of collagen metabolism, against collagen hypometabolism caused by aging.

DISCLOSURE OF INVENTION

Accordingly, an object of the present invention is to provide a collagen metabolism ameliorant, that is, a collagen metabolism ameliorating agent efficacious against collagen hypometabolism caused by aging or diseases accompanied with an abnormal accumulation of collagen, such as hepatic and pulmonary fibroses, keloid, hypertrophic scar, scleroderma, or fibrosis in the scalp, and further to provide useful hair growth stimulants and skin aging inhibitors.

The present inventors, as a result of assiduous studies for achieving the above-described object, have found that MSE has an action of promoting the production of the procollagenase, and accomplished the present invention.

Namely, the present invention relates to a collagen metabolism ameliorant containing MSE as an active ingredient and its use.

The collagen metabolism ameliorant according to the present invention can be compounded with a known ingredient according to its use object and prepared into a dosage form suited for peroral administration or parenteral administration such as injection, percutaneousness or the like, by a usual process. This ameliorant is administered perorally or parenterally, such as by injection, percutaneousness or the like, to the human body.

As a dosage form for peroral administration, mention may be made of solid preparations such as tablets, granules, powders, particulates, hard gelatine capsules and the like, and in addition, solutions such as syrups, elixirs, elastic capsules and the like.

Injections are prepared by dissolving or emulsifying MSE in physiological salt solution or a lipid diluting agent such as vegetable oils, oil emulsions, glycols or the like, and encapsulating germfreely into ampuls or vials.

Percutaneous medicaments include ointments, lotions, cataplasms, gels, creams, solutions, aerosols, baths, patches and the like.

The collagen metabolism ameliorant according to the present invention is administered perorally or parenterally.

In the case of a disease accompanied with an abnormal accumulation of collagen in an organ, such as hepatic fibrosis, pulmonary fibrosis and the like, the collagen metabolism ameliorant of the present invention is administered perorally or by injection, and in the case of a disease accompanied with an abnormal accumulation of collagen in skin, such as keloid, hypertrophic scar, fibrosis in the scalp, and the like, it is administered percutaneously or by a regional injection.

Alternatively, in the case of collagen hypometabolism caused by aging, the collagen metabolism ameliorant according to the present invention is administered perorally or percutaneously.

Though the dosage depends upon the age, weight, conditions of a patient to be administered, dosage form and the like, in the case of adults, generally a dose of 0.1–1,000 mg as MSE and 1–3 doses a day are administered.

For example, in the case of a disease accompanied with an abnormal accumulation of collagen in an organ, such as hepatic fibrosis, pulmonary fibrosis and the like, a dose of 30–1,000 mg by peroral or injection administration is appropriate, while in the case of a disease accompanied with an abnormal accumulation of collagen in skin, such as keloid, hypertrophic scar, fibrosis of the scalp and the like, or a skin with collagen hypometabolism caused by aging, a dose of 0.1–50 mg by percutaneous administration is appropriate.

Alternatively, the collagen metabolism ameliorant according to the present invention can be used as a hair growth stimulant and a skin aging inhibitor.

The hair growth stimulant can be compounded with a known material according to a usual process and prepared into preventives for hair falling-off, hair-restorers, and further into the form of a hair-restoring cosmetics such as shampoo, rinse, hair tonic, hair lotion, hair cream, hair conditioners, hair gel, hair mist, hair foam and the like.

In the hair growth stimulant, MSE is compounded in an amount of 0.001–10.0% by weight (hereinafter abbreviated as "wt. %"), preferably 0.01–5.0 wt. %, based on the total amount.

The skin aging inhibitor can be compounded with a known material according to a usual process and prepared into dermal cosmetics such as wrinkle preventives, ointments and, further into the form of skin lotion, skin milk, skin cream, pack or the like.

In the skin aging inhibitor, MSE is compounded in an amount of 0.001–10.0 wt. %, preferably 0.01–5.0 wt. %, based on the total amount.

Additionally, as the collagen metabolism ameliorant according to the present invention, though MSE is mentioned as the above, pharmacologically allowable salts thereof also can be likewise utilized. Best mode for carrying out the invention In the outset, assessments of MSE, etc. will be described with respect to pharmacological functions and effects, and then assessments regarding the after-described examples and comparative examples will be made by comparative experiments.

I. Action of MSE for promoting procollagenase production.

1) Abbreviations.

The following abbreviations used in the experiments have the under-noted meanings.

HF medium: a medium prepared by dissolving 10.6 g of Ham's F12 powdery medium (manufactured by Nissui Pharmaceutical Co.) in refined water.

HF-AV medium: a medium prepared by admixing 1 liter of the HF medium with 1.76 g of a powdery Eagle's amino acid vitamin medium (manufactured by Nissui Pharmaceutical Co.), 1.6 g of sodium carbonate, 50 mg of streptomycin sulfate and 60 mg of kanamycin sulfate and then blowing carbon dioxide gas thereinto to adjust the pH to about 7.

TRIS: tris(hydroxymethyl)aminomethane.

MES buffer solution: a buffer solution prepared by adjusting the pH of a 50 mM 2-(N-morpholino)ethane sulfonic acid monohydrate aqueous solution containing a 0.5M NaCl, a 1 mM $CaCl_2$ and 0.05% by volume of BRIJ-35 (the trademark of polyoxyethylene laurylalcohol) to 6.5 at 4° C. with a TRIS aqueous solution.

Acetic acid buffer solution: a buffer solution prepared by adjusting the pH of a 25 mM acetic acid aqueous solution containing a 0.5M NaCl, a 1 mM $CaCl_2$ and 0.05% by volume of BRIJ-35 to 4.5 at 4° C. with a TRIS aqueous solution.

MES-A buffer solution: a buffer solution prepared by adjusting the pH of the MES buffer solution to 7 at 4° C. with a TRIS aqueous solution.

MES-B buffer solution: a buffer solution prepared by mixing the MES buffer solution with the acetic acid buffer solution and adjusting the pH to 6.2 at 4° C.

MES-C buffer solution: a buffer solution prepared by mixing the MES buffer solution with the acetic acid buffer solution and adjusting the pH to 5.2 at 4° C.

Buffer solution for measurement: a buffer solution prepared by adjusting the pH of a 50 mM TRIS aqueous solution containing a 0.2M NaCl, a 5 mM $CaCl_2$, 0.05% by volume of BRIJ-35 and 0.02 w/v % of $NaN_3$ to 7.5 at room temperature with hydrochloric acid.

2) Procedure.

A test was carried out using anchorage independent cell strain which is derived from a human fibrosarcoma cell strain HT 1080 (ATCC CCL121) and growable in a serum-free, protein-free medium (referred to as "human fibrosarcoma cell strain HT-P11".). Namely, the above-described human fibrosarcoma cell strain HT 1080 (ATCC CCL1211) was cultured in the presence of serum in a flask having a base area of 25 $cm^2$ and the medium was replaced by the HF-AV medium. Replacing a fifth to half part of the cultured suspension with a fresh HF-AV medium every 3–4 days, the culture was continued in a serum-free, protein-free medium. The thus grown cells were used. The cells were pre-cultured as below to prepare a cell suspension which was then tested.

The human fibrosarcoma cell strain HT-P11 was suspended with a density of $1\times10^5$ cells/ml in the HF-AV medium. Flasks (each having a base area of 75 $cm^2$) were charged, respectively, with 20 ml of the resulting suspension, and stationarily cultured at 37° C. for 3 days in a 95% air/5% carbon dioxide gas atmosphere.

After culturing for 3 days, the cells were collected by centrifugation (at 600 rpm for 10 min.). The obtained cells were suspended in the HF-AV medium to prepare a cell suspension with a density of $7\times10^4$ cells/ml.

Two milliliters each of the above cell suspension was laid on a 6 well plate (with a base area of 9.4 $cm^2$) and cultured at 37° C. for 1 day in a 95% air/5% carbon dioxide gas atmosphere. Then, a 10 mM conc. MSE aqueous solution was diluted into a 600 μM concentration with the HF-AV medium. After sterilizing by filtering with a nitrocellulose membrane having a pore size of 0.2 μm (the trademark "DISMIC-25" manufactured by Advantec Toyo Co.), 0.4 ml each of the above solution was added to culture solutions and cultured for 13 days in a 95% air/5% carbon dioxide gas atmosphere. After completing culturing, 1 part by volume of a 10 vol. % BRIJ-35 aqueous solution was added to 200 parts by volume of the culture solution. Then, the cells were separated by centrifugation (at 600 rpm for 10 min.) and a culture supernatant liquor was obtained.

Then, 0.5 ml of the culture supernatant liquor was admixed with 0.5 mol of the MES-A buffer solution and the mixture was charged into a column loaded with 0.5 ml of zinc chelating SEPHAROSE 6B™ (manufactured by Pharmacia) equilibrated by the MES-A buffer solution. By 4 repetitive flows of 1 ml each of the MES-B buffer solution through the column, collagenase inhibitors were eluted from the column and removed.

Then, by 2 repetitive flows of 1 ml each of the MES-C buffer solution, eluting solution was collected and 2 ml of procollagenase solution were obtained.

After adjusting the pH value of the procollagenase solution to about 7 with a 1N-NaOH, the volume of the solution was increased to 2.5 ml by adding the MES-A buffer solution thereto. Then, using the buffer solution for measurement, a solution containing about 0.1–0.7 unit/ml of the procollagenase was prepared as a test liquid.

Then, 50 μl of the test liquid were admixed with 20 μl of a trypsin solution ("Type 12" manufactured by Sigma Chemical, adjusted into a 1 mg/ml concentration with the buffer solution for measurement) and, after incubating at 35° C. for 5 min., further admixed with 30 μl of a soybean trypsin inhibitor solution ("No. 24020" manufactured by Merck, was adjusted into a 3 mg/ml concentration with the buffer solution for measurement) to inactivate the trypsin and a collagenase solution was obtained.

Using a type-I collagen labeled with fluorescein isothiocyanate (hereinafter abbreviated as "FITC") (a 1 mg/ml conc. FITC/collagen acetic acid solution, manufactured by Cosmo Bio Co.) as a substrate solution, the activity (unit/ml) of the above collagenase solution was determined in accordance with the following procedure.

3) Determination of activity of collagenase using an FITC-collagen acetic acid solution as a substrate.

(3-1) Reagent and material.

① 0.1 w/v % FITC-collagen acetic acid solution (manufactured by Cosmo Bio Co., Ltd. Tokyo, Japan).

② 0.1M TRIS buffer solution: a buffer solution prepared by adjusting the pH of a 0.1M TRIS aqueous solution containing a 0.4M NaCl, 10 mM $CaCl_2$ and 0.04% $NaN_3$ in the final concentration, to 7.5 at room temperature with hydrochloric acid.

③ 0.17M TRIS hydrochloric acid buffer solution: a buffer solution prepared by adjusting the pH of a 0.17M TRIS aqueous solution containing a 0.67M NaCl to 9.5 at 4° C. with hydrochloric acid.

④ 70% ethanol-30% 0.17M TRIS hydrochloric acid buffer solution: a mixed buffer solution containing ethanol and a 0.17M TRIS hydrochloric acid buffer solution at a ratio of 7 to 3.

(3-2) Determination of activity of collagenase.

① Fifty μl of a 0.1% FITC-labeled collagen solution were added dropwise to 50 μl of the 0.1M TRIS buffer solution and the mixture was gently stirred to prepare a substrate solution.

② One hundred μl of the above collagenase solution were admixed with 100 μl of the substrate solution, and the mixture was gently stirred and then reacted at 35° C. for 16 hours.

In parallel with the above, using the buffer solution for measurement instead of the collagenase solution, admixed with the substrate solution in the same manner, a control sample used for calculation of the activity of the collagenase was prepared.

③ After the reaction was completed, 10 μl of a 50% ethanol containing an 80 mM o-phenanthroline were added to stop the reaction, and then 200 μl of the buffer solution for measurement were further added followed by standing at 35° C. for 1 hour to provide a collagenase solution test sample.

The control sample prepared by admixing the buffer solution for measurement with the substrate solution was left to stand for 1 hour and then heated at 80° C. for 10 minutes to provide a total test sample. The same sample except that the heating was not conducted was referred to as a blank test sample.

④ After standing for 1 hour, each test sample was admixed with 400 μl of the 70% ethanol-30% 0.17M TRIS hydrochloric acid buffer solution and stirred vigorously with vortices.

⑤ After stirring, centrifuging at 10,000 rpm for 3 minutes, the obtained supernatant was measured for a fluorescence intensity (Em 520 nm/Ex 495 nm).

⑥ From the fluorescence intensity of each test sample, the activity of the collagenase was found by the following formula:

$$\text{Activity of collagenase (unit/ml)} = \frac{F_S - F_B}{F_T - F_B} \times \text{amount of used substrate (50 μg)} \times \frac{1}{\text{reaction time (16 hrs.)}} \times \frac{1}{\text{amount of sample (50 μl)}}$$

where, $F_S$: fluorescence intensity of collagenase solution test sample, $F_T$: fluorescence intensity of total test sample, and $F_B$: fluorescence intensity of blank test sample.

With respect to the collagenase produced from the procollagenase by the aforementioned trypsin treatment, an amount enough to decompose 1 μg/min. of the type-I collagen (FITC/collagen) at 35° C., is assumed to be a unit procollagenase and the production of the procollagenase (unit/ml of culture solution) was found (let this value be X).

On the other hand, as a control experiment, refined water in lieu of the MSE aqueous solution was added and the production of the procollagenase (unit/ml culture solution) in the absence of MSE was found by the same procedure as the above (let this value be Y).

Then, from these values, a procollagenase production promotion rate (%) was calculated by the following equation.

$$\text{Procollagenase production promotion rate (\%)} = \frac{X - Y}{Y} \times 100$$

4) Test result

The results are shown in Table 1.

TABLE 1

| Test compound | Production of procollagenase (unit/ml of culture solution) | Production promotion rate (%) |
|---|---|---|
| No additives (control) | 3.7 ± 0.2 | — |
| MSE | 7.9 ± 0.7** | 114 |

The data shows a mean value ± standard error (N = 3).
**As P < 0.01, significantly different as compared with no additives (control) (by Duncan's method).

As is clear from Table 1, MSE promoted the production of the procollagenase.

II. Effect of MSE in medical treatment for hepatic fibrosis.

A model animal of hepatic fibosis was prepared and tested.

1) Procedure.

A 2 ml/kg dose of an equivalent mixture of carbon tetra-chloride ($CCl_4$) and olive oil was administered hypodermically to the back of male rats of Wistar origin (5 weeks old; a weight of 122–134 g; and 5 rats/group) twice a week (on Monday and Thursday) for 10 weeks to produce rats of hepatic fibrosis. A 3 ml/kg dose of a 66.6 mg/ml conc. MSE aqueous solution was administered perorally once a day for continual 7 weeks (except Sundays) from the 4th week after the commencement of the $CCl_4$ administration.

Then, the whole blood was gathered from the abdominal aorta and collected in a test tube treated with heparin. This was centrifuged to obtain blood plasma. The blood plasma was stored at −80° C. until the under-mentioned biochemical examinations.

Further, after gathering the whole-blood, the liver was extracted, weighed and divided into halves under an ice-chilled condition. Then, one of the halves was frozen at −80° C. for quantification of hydroxyproline (hereinafter abbreviated as "Hyp") in the liver and the other half was fixed with a 10% formaline solution for a histological examination.

On the other hand, there were provided, as an untreated group, a group of the rats of hepatic fibrosis administered with 3 ml/kg of refined water in lieu of the MSE aqueous solution according to the same schedule as the above and, as a group of normal rats, a group bred for 10 weeks without administering $CCl_4$ and the MSE aqueous solution. Blood-gathering and liver-extraction were conducted on these groups in the same manner as the above.

Then, using the above each liver and blood plasma, the Hyp in the liver and blood were quantified. Additionally, the Hyp is an index of the quantity of the collagen [Methods of Biochemical Analysis, Vol. 15, p. 25 (1967)]. Further, biochemical examinations of the blood plasma [refer to the under-described items (b)-(h)] and histological examinations of the liver [refer to the under-described item (i)], as indices of liver injury, were conducted.

Each examination item and examination method are as follows.

(a) Quantities of the Hyp in liver and blood.

(a-1) Quantity of the Hyp in a liver: about 100 mg of a liver were weighed precisely and added with 250 μl of physiological salt solution. Then, the liver was disintegrated by agitating vigorously (at 28,000 rpm for 30 seconds) with a homogenizer (PHYSCOTRON™, manufactured by Niti-On Medical and Physical Instruments Mfg. Co.).

The obtained suspension was centrifuged (at 5,000 rpm for 10 min.) and separated into a supernatant sample and a precipitation sample. By adding a 6N hydrochloric acid, each sample was increased to 2 ml and hydrolyzed at 110° C. for 24 hours. The hydrolyzate solution was centrifugally condensed to remove hydrochloric acid therefrom and the condensate was dissolved in a 0.01N hydrochloric acid.

The obtained solution was quantified according to a determination method of amino acids by a high-performance liquid chromatography with a post-column derivatization [Proceedings of the National Academy of Sciences of the U.S.A., Vol. 72, No. 2, p. 619 (1975)] to find quantities of the Hyp in the supernatant sample and precipitation sample, respectively. Then, a quantity of the Hyp per unit weight of the liver (μmol/g of liver) was calculated from the total quantity of the Hyps in the supernatant sample and precipitation sample and the weight of the liver.

(a-2) Quantity of the Hyp in blood: 100 μl of blood plasma was admixed with 100 μl of a 5 w/v % sulfo-salicylic acid aqueous solution under an ice-chilled condition and centrifugally separated (10,000 rpm; for 3 min.) to obtain a supernatant liquor. The Hyp in the supernatant liquor was quantified according to the above-mentioned determination method of amino acids (μmol/1).

(b) Quantity of glutamic-pyruvic transaminase (hereinafter abbreviated as "GPT"):

(b-1) Reagent.

① 0.1M phosphate buffer solution (pH: 7.4): 7.2 g of disodium hydrogen phosphate dihydrate (guaranteed reagent) and 1.36 g of potassium dihydrogen phosphate (guaranteed reagent) were dissolved in water being added up to 500 ml.

② Substrate solution for GPT: 29.2 mg of α-ketoglutaric acid and 1.78 g of DL-alanine were put into a small beaker and dissolved by adding 15 ml of the 0.1M phosphate buffer solution thereto. After adjusting the pH to 7.4 with a small amount (0.5~0.7 ml) of 1N-NaOH, the solution was transferred into a measuring flask and the 0.1M phosphate buffer solution was added up to 100 ml. Then, after adding about 1 ml of chloroform, the solution was refrigerated.

③ Color reagent: precisely weighed 20.0 mg of 2,4-dinitro-phenylhydrazine were dissolved in 7.0 ml of hydrochloric acid and then water was added up to 100 ml.

④ 0.4N-NaOH solution: 16 g of NaOH were dissolved in water being added up to 1,000 ml.

⑤ 20 mM pyruvic acid standard solution: 224 mg of lithium pyruvate were dissolved in the 0.1M phosphate buffer solution being added up to 100 ml. Then, after adding about 1 ml of chloroform, the solution was refrigerated. The titer was checked by iodometry.

⑥ 2 mM pyruvic acid standard solution: a checked 20 mM pyruvic acid standard solution was diluted to 2 mM with the 0.1M phosphate buffer solution.

(b-2) Calibration curve.

① Into 7 test tubes, the 2 mM pyruvic acid standard solution, substrate solution for GPT and water were put in amounts as shown in Table 2. After adding 1.0 ml of a color reagent, each test tube was left to stand at room temperature for 20 minutes.

② Ten ml of the 0.4N-NaOH solution were added to each test tube while mixing well. After standing the test tubes at room temperature for 30 minutes, the absorbance at 505 nm was determined using water as a control.

③ The absorbance of No. 1 test tube was subtracted from the absorbance of No. 2 and following test tubes, and a calibration curve was plotted for absorbency on the abscissa axis against Reitman-Frankel unit on the ordinate axis.

TABLE 2

| Test tube No. | 1 | 2 | 3 | 4 | 5 | 6 | 7 |
|---|---|---|---|---|---|---|---|
| 2 mM pyruvic acid (ml) | 0 | 0.05 | 0.10 | 0.15 | 0.20 | 0.25 | 0.30 |
| Substrate soln. (ml) | 1.0 | 0.95 | 0.90 | 0.85 | 0.80 | 0.75 | 0.70 |
| Refined water (ml) | 0.2 | 0.2 | 0.2 | 0.2 | 0.2 | 0.2 | 0.2 |
| Reitman-Frankel unit | 0 | 12 | 26 | 41 | 58 | 75 | 93 |

(b-3) Measurement of test sample.

① Test tubes A and B were prepared. One ml. of the substrate solution for GPT was put into the tube A and held at a temperature of 37° C.

② Two tenth ml of a blood plasma test sample diluted appropriately with the 0.1M phosphate buffer solution was put into the tubes A and B, respectively, mixed well and held exactly at a temperature of 37° C. for 30 minutes.

③ After adding 1.0 ml of the color reagent to the above solution and mixing, the solution was reacted at room temperature for 20 minutes.

④ As a blank test, 1.0 ml of the substrate solution and 1.0 ml of the color reagent were added to the test tube B and mixed. Immediately thereafter, 0.2 ml of the test sample was added and the test tube B was left to stand at room temperature for 20 minutes.

⑤ Ten ml of the 0.4N-NaOH solution were added to the test tubes A and B, respectively, while mixing well. After standing the test tubes at room temperature for 30 minutes, the absorbance at 505 nm was determined using water as a control.

⑥ The absorbance of the blank test tube B was subtracted from the absorbance of the test tube A, and a Reitman-Frankel unit was obtained from the calibration curve.

(c) Quantity of glutamic-oxaloacetic transaminase (hereinafter abbreviated as "GOT"):

(c-1) Reagent.

① As to 0.1M phosphate buffer solution (pH: 7.4), color reagent, 0.4N-NaOH solution, 20 mM pyruvic acid standard solution and 2 mM pyruvic acid standard solution, the same solutions as those in the examination system for GPT quantity (b-1) were employed.

② Substrate solution for GOT: 29.2 mg of α-ketoglutaric acid and 2.66 g of L-Aspartic Acid were put into a small beaker and dissolved by adding about 20 ml of 1N-NaOH thereto. After adjusting the pH to 7.4, the solution was transferred into a measuring flask and the 0.1M phosphate buffer solution was added up to 100 ml. Then, after adding about 1 ml of chloroform, the solution was refrigerated.

(c-2) Calibration curve.

Into 7 test tubes, the 2 mM pyruvic acid standard solution, substrate solution for GOT and water were put in amounts as shown in Table 3. Procedures following the above were conducted in the same manner as the preparation of the calibration curve for GPT in b-2 above.

TABLE 3

| Test tube No. | 1 | 2 | 3 | 4 | 5 | 6 | 7 |
|---|---|---|---|---|---|---|---|
| 2 mM pyruvic acid (ml) | 0 | 0.05 | 0.10 | 0.15 | 0.20 | 0.25 | 0.30 |
| Substrate soln. (ml) | 1.0 | 0.95 | 0.90 | 0.85 | 0.80 | 0.75 | 0.70 |
| Refined water (ml) | 0.2 | 0.2 | 0.2 | 0.2 | 0.2 | 0.2 | 0.2 |
| Reitman-Frankel unit | 0 | 11 | 24 | 40 | 60 | 82 | 112 |

(c-3) Measurement of test sample.

The measurement of test samples was conducted in the same manner as that described in b-3 above, except that the substrate solution for GPT was replaced by the substrate solution for GOT.

(d) Quantity of γ-glutamyl transpeptidase (hereinafter abbreviated as "γ-GTP"):

(d-1) Reagent (γ-GTP Test Pack, manufactured by Sankyo Co.)

① Substrate buffer solution: contents are 4.6 mM of γ-glutamyl-p-nitroanilide, 28.3 mM of glycylglycine, 30 mM of barbital Na salt, 30 mM of sodium acetate and a surface active agent.

② Reaction stopper solution: an 18.7 mM HCl.

③ Standard solution.

(d-2) Measurement of test sample.

① Test proper: 1.0 ml of the substrate buffer solution was put into a test tube, heated at 37° C. for 5 minutes, admixed with 50 μl of blood plasma and held exactly at 37° C. for 30 minutes. Then, after admixing 5.0 ml of the reaction stopper solution, the absorbance ($E_A$) at 410 nm was determined using water as a control.

② Sample blank test: 1.0 ml of the substrate solution was put into a test tube, heated at 37° C. for 30 minutes, then admixed with 5.0 ml of the reaction stopper solution and 50 μl of blood plasma. The absorbance ($E_B$) was determined in the same manner as the $E_A$ in the above ①.

③ Standard solution: 1.0 ml of the standard solution was admixed with 5.0 ml of the reaction stopper solution and the absorbance ($E_S$) was determined in the same manner as the $E_A$ in the above ①.

④ Calculation: when 1 μM of p-nitroaniline per 1 liter of blood plasma is liberated at 37° C. for 1 minute, the enzyme activity of the blood plasma is defined as 1 U/liter. The standard solution has an enzyme activity equivalent to 250 units of blood plasma γ-GTP. Hence, the activity of the blood plasma γ-GTP was found by the following equation:

$$\text{Blood plasma } \gamma\text{-GTP activity (U/l)} = \frac{E_A - E_B}{E_S} \times 250$$

(e) Quantity of gross bilirubin: determined according to the Malloy-Evelyn's method (Journal of Biological Chemistry, 119, 481, 1937) (m9/dl).

(f) Quantity of alkaline phosphatase: this was determined according to the Bessey-Lowry's method (Journal of Biological Chemistry, 164, 321, 1964) (unit/l).

(g) Thymol turbidimetric test value (hereinafter abbreviated as "TTT"):

(g-1) Reagent:

① Thymol reagent: 1,100 ml of water were boiled for 5 minutes to expel $CO_2$ therefrom. When the temperature descended to about 95° C., 300 ml were poured into a 1 liter Erlenmeyer flask containing 6 g of colorless thymol crystals. The flask was stoppered and rotated to dissolve the thymol crystal. To the solution, 3.09 g of barbital, 1.69 g of the barbital Na-salt and 700 ml of the remaining water having a temperature of about 95° C. were further added. The flask was again stoppered and rotated for about 5 minutes to mix vigorously. Then, after leaving it cooling at room temperature, the content was transferred into a 1 liter measuring flask and water was added up to the graduation line. The content was again transferred back to the Erlenmeyer flask and 1 g of thymol was added and mixed vigorously until it turned transparent. After being left at room temperature overnight, it was filtrated and the pH was corrected to 7.55±0.03.

② Standard solution: a 100 ml measuring flask was washed well with water and swished off as much the water as possible. Into the flask, 3.0 ml of a 1.15 g/dl barium chloride aqueous solution was introduced accurately so as not to touch the wall of the flask. The flask was steeped in water at 10° C., and a 0.2N-$N_2SO_4$ aqueous solution cooled down to 10° C. was added flowing down on and along the inside wall of the neck of the flask as quickly as possible but not foaming. After adding up to the 100 ml graduation line, the flask was turned end for end to effect thorough mixing. Within 10 minutes, the absorbency at 650–660 nm was read using water as a control, which was assumed to be 20 U of Kunkel. The plot of this unit was connected with the origin by a straight line to depict a calibration line.

(g-2) Measurement of test sample.

Into a test tube, 0.1 ml of blood plasma was put and 6.0 ml of the reagent was added and mixed well. The test tube was placed in a water bath at 25°±3° C. for minutes. Then, the turbidity at a wavelength of 660 nm was determined using the reagent as a blank test sample.

(h) Zinc sulphate turbidimetric test value (hereinafter abbreviated as "ZTT"):

(h-1) Reagent:

① Zinc sulfate reagent: 1 liter of water was boiled for 10 minutes to expel $CO_2$ therefrom. While it was hot, 302 mg of barbital, 190 mg of the barbital Na-salt were dissolved thereinto. To this solution, 5.0 ml of a newly prepared 0.480 g/dl zinc sulfate aqueous solution were added and then water was further added up to 1 liter.

② Standard solution: a standard solution was prepared in the same manner as TTT. The calibration curve and unit were also the same as the above.

(h-2) Measurement of test sample:

One tenth ml part of blood plasma was put into a test tube and 6.0 mol of the reagent were tossed therein and mixed well. The test tube was placed in a water bath at 25°±3° C. for 30 minutes and then the turbidity at a wavelength of 660 nm was determined using the reagent as a blank test sample.

(i) Histological examination of liver: a liver was sliced according to a usual method and, after staining with hematoxylin-eosin, it was microscopically observed.

2) Test result.

The quantities of the Hyp in the liver and blood as well as biochemical examination values of the blood plasma, as an index of liver injury, are shown in Table 4.

TABLE 4

| Exam. item | Group of normal rats | Rats of hepatic fibrosis induced by $CCl_4$ | |
|---|---|---|---|
| | | Untreated group | MSE administered group |
| a-1 | 1.72 ± 0.63 | 10.0 ± 1.5 | 6.79 ± 0.82* |
| a-2 | 27.6 ± 2.3 | 30.6 ± 1.1 | 39.1 ± 3.6* |
| b | 45.2 ± 3.8 | 948 ± 92 | 537 ± 182** |
| c | 85 ± 6.8 | 2170 ± 184 | 875 ± 324** |
| d | 1.8 ± 0.6 | 17.6 ± 0.7 | 14.4 ± 1.7* |
| e | <0.10 | 0.36 ± 0.02 | 0.26 ± 0.05* |
| f | 317 ± 13 | 1270 ± 90 | 956 ± 114** |
| g | 0.10 ± 0.03 | 0.26 ± 0.06 | 0.18 ± 0.13 |
| h | 0.28 ± 0.08 | 0.78 ± 0.11 | 0.26 ± 0.07** |

The data shows a mean value ± standard error (n = 5).
*Significantly different with a risk factor $p < 0.1$ as compared with the untreated group (by Duncan's method).
**Significantly different with a risk factor $p < 0.01$ as compared with the untreated group (by Duncan's method).

As shown in Table 4, the MSE administered group had significantly a low Hyp content in the liver and significantly a high Hyp content in blood, as compared with the untreated group. This shows that the collagen metabolism ameliorant of the present invention promotes the production of the procollagenase with the consequence that the decomposition of the collagen in the fibrotic hepatic tissue is promoted, resulting in isolation of the Hyp in blood.

Further, the biochemical examination values of the blood plasma of the MSE administered group are significantly low with respect of GPT, GOT, γ-GTP, gross bilirubin, alkaline phosphatase and ZTT, as compared with those of the untreated group. From this fact, it can be said that the collagen metabolism ameliorant of the present invention ameliorated a liver injury accompanied with hepatic fibrosis.

On the other hand, in a histological examination of the liver, it was observed that the MSE administered group mitigated a liver-injury-based, diffuse hepatocyte vacuolization, cholangiolar hyperplasia and cholangioepithelial cytogenesis, respectively, as compared with the untreated group. This fact also proves that the collagen metabolism ameliorant of the present invention is efficacious against a liver injury accompanied with hepatic fibrosis.

The present invention will be explained in more detail hereinafter by way of examples, comparative examples and comparative experiments.

III. Acute toxicity.

An acute toxicity was examined as follows:

To 5 male mice of ICR strain (5 weeks old; a weight of 24~28 g), a 25 g/ml conc. MSE aqueous solution that had been prepared by dissolving MSE in refined water was perorally administered once in a dose of 0.2 ml/kg of the body weight (5 g/kg of the body weight, as MSE).

Then, the mice were observed for 7 days and no deaths by administration of MSE were recognized.

IV. Skin irritative test.

Using male rabbits of Japanese native strain (a weight of about 3 kg), a skin irritative test was conducted in accordance with the Draize method [Appraisal of the Safety of Chemicals in Foods, Drugs and Cosmetics, p.46 (1959) edited and published by the Editorial Committee, Association of Food & Drug Official of U.S.A.].

An abraded region (injured skin) was produced on the hair-trimmed back of the rabbits. An adhesive plaster for a patch test (RIBBON-AID™ of 1.2 cm×1.6 cm, manufactured by Liba-Tape & Co., Ltd.) was impregnated with 0.1 ml of a 1 wt. % MSE aqueous solution that had been prepared by dissolving MSE in refined water and attached onto the injured skin and a normal skin, respectively. After 24 hours, the plaster was detached to observe erythematic and edematous conditions of the skins. After 48 hours from detaching of the plaster, the same observation was made. Erythematic scores and edematous scores were recorded based on the criteria of assessment shown in Table 5.

TABLE 5

| Criterion of assessment | Erythematic score | Edematous score |
|---|---|---|
| No erythema nor edema | 0 | 0 |
| Very slight erythema or edema | 1 | 1 |
| Mild erythema or edema | 2 | 2 |
| Medium erythema or edema | 3 | 3 |
| Severe erythema or edema | 4 | 4 |

Based on the above scores and the following equation, primary irritant scores were calculated.

$$\text{Primary irritant score}=(A_{24}+A_{48})/2+(B_{24}+B_{48})/2+(X_{24}+X_{48})/2+(Y_{24}+Y_{48})/2$$

where each symbol has the following means:

$A_{24}$: an erythematic score after 24 hours from attaching the plaster onto the normal skin, $A_{48}$: an erythematic score after 48 hours from detaching the plaster from the normal skin, $B_{24}$: an erythematic score after 24 hours from attaching the plaster onto the injured skin, $B_{48}$: an erythematic score after 48 hours from detaching the plaster from the injured skin, $X_{24}$: an edematous score after 24 hours from attaching the plaster onto the normal skin, $X_{48}$: an edematous score after 48 hours from detaching the plaster from the normal skin, $Y_{24}$: an edematous score after 24 hours from attaching the plaster onto the injured skin, and $Y_{48}$: an edematous score after 48 hours from detaching the plaster from the injured skin.

Then, irritation degrees of the test compounds were appraised based upon the primary irritative scores and the criteria shown in Table 6.

TABLE 6

| Primary irritative score | Appraisal |
|---|---|
| 0~less than 2 | mild irritation |
| 2~less than 5 | moderate irritation |
| 5 or more | severe irritation |

As the results of the skin irritative test, the primary irritative score was found to be zero which was appraised as light irritation.

The present invention will be explained in more detail hereinafter by way of examples, comparative examples and comparative experiments.

EXAMPLES 1~3

MSE was added to and dissolved in the hydrophilic ingredients shown in Table 7 in an amount of 0.1 wt. % (Example 1), 0.5 wt. % (Example 2) or 4.0 wt. % (Example 3). Then, the resulting solution was mixed with an ethanol solution of the lipophilic ingredients shown in Table 7 and stirred to disperse therein. Thus, oily hair tonics were prepared.

TABLE 7

| Starting ingredient | Content (wt. %) |
|---|---|
| (Hydrophilic ingredient) | |
| Glycerin | 5.0 |
| Aromatic | 0.1 |
| Refined water | balance |
| (Lipophilic ingredient) | |
| Olive oil | 5.0 |
| Isopropyl myristate | 2.0 |
| Isopropylmethylphenol | 0.05 |
| Polyoxyethylene nonylphenylether (20 E.O.) | 0.5 |
| Methyl parahydroxybenzoate | 0.1 |

Comparative Examples 1~3

Oily hair tonics were prepared in the same manner as Example 1, except that MSE was replaced by 0.1 wt. % of red pepper tinctures (Comparative Example 1), 5.0 wt. % of Japanese swertia extracts (Comparative Example 2) or 0.1 wt. % of ethyl nicotinate (Comparative Example 3).

EXAMPLES 4 AND 5

MSE was added to and dissolved in the hydrophilic ingredients shown in Table 8 in an amount of 0.2 wt. % (Example 4) or 3.0 wt. % (Example 5). Then, the resulting solution was mixed with the lipophilic ingredients shown in Table 8 at 80° C. While stirring, the resultant was cooled down to 50° C. where an aromatic ingredient was added and stirring was further continued until 30° C. was reached. Thus, hair creams were prepared.

TABLE 8

| Starting ingredient | Content (wt. %) |
|---|---|
| (Hydrophilic ingredient) | |
| Methyl parahydroxybenzoate | 0.2 |
| Glycerin | 5.0 |
| Refined water | balance |
| (Lipophilic ingredient) | |
| Liquid paraffin | 30.0 |
| Stearic acid | 5.0 |
| Cetanol | 5.0 |
| Sorbitan monooleate | 3.0 |
| Polyoxyethylene sorbitan monooleate (20 E.O.) | 3.0 |
| Isopropylmethylphenol | 0.1 |
| (Aromatic ingredient) | 0.2 |
| Aromatic | |

Comparative Examples 4~6

Hair creams were prepared in the same manner as Example 4, except that MSE was replaced by 0.1 wt. % of red pepper tinctures (Comparative Example 4), 0.1 wt. % of biotin (Comparative Example 5) or 2.0 wt. % of panthenol (Comparative Example 6).

EXAMPLES 6~8

MSE was added to and dissolved in the hydrophilic ingredients shown in Table 9 in an amount of 0.1 wt. % (Example 6), 1.0 wt. % (Example 7) or 4.0 wt. % (Example 8). After dissolving, the resulting solution was admixed with the lipophilic ingredients shown in Table 9 which had been homogeneously dissolved by heating and stirring at 75° C. for 5 minutes. The mixture was stirred into a homogeneous dispersion which was then cooled down to 30° C. while stirring. Thus, skin milks were prepared.

TABLE 9

| Starting ingredient | Content (wt. %) |
|---|---|
| (Hydrophilic ingredient) | |
| Sodium N-lauroylglutamate | 2.0 |
| Methyl parahydroxybenzoate | 0.2 |
| Refined water | balance |
| (Lipophilic ingredient) | |
| Liquid paraffin | 20.0 |
| Stearic alcohol | 5.0 |
| Isopropyl myristate | 1.5 |

Comparative Examples 7 and 8

Skin milks were prepared in the same manner as Example 6, except that MSE was replaced by 5.0 wt. % of γ-oryzanol (Comparative Example 7) or 0.1 wt. % of ethyl nicotinate (Comparative Example 8).

EXAMPLES 9 AND 10

MSE was added to the hydrophilic ingredients shown in Table 10 which had been dissolved by heating at 80° C., in an amount of 0.2 wt. % (Example 9) or 4.0 wt. % (Example 10). After dissolving, the resulting solution was admixed with the lipophilic ingredients shown in Table 10 which had been dissolved by heating at 80° C. Then, the mixture was stirred into a homogeneous dispersion which was then cooled down to 30° C. while stirring. Thus, skin creams were prepared.

TABLE 10

| Starting ingredient | Content (wt. %) |
|---|---|
| (Hydrophilic ingredient) | |
| Glycerin | 5.0 |
| Methyl parahydroxybenzoate | 0.1 |
| Refined water | balance |
| (Lipophilic ingredient) | |
| Squalane | 10.0 |
| Olive oil | 10.0 |
| Solid paraffin | 5.0 |
| Cetanol | 4.0 |
| Sorbitan monostearate | 2.0 |
| Polyoxyethylene sorbitan monostearate (20 E.O.) | 2.0 |

Comparative Examples 9 and 10

Skin creams were prepared in the same manner as Example 9, except that MSE was replaced by 5.0 wt. % of panthenol (Comparative Example 9) or 0.1 wt. % of biotin (Comparative Example 10).

EXAMPLE 11

The lipophilic ingredients shown in Table 11 were dissolved by heating at 80° C., and the hydrophilic ingredients shown in Table 11 which had been dissolved by heating at 80° C. were added thereto and mixed by stirring. Then, while stirring, the mixture was gradually cooled down to room temperature. Thus, a water-absorbing ointment was prepared.

TABLE 11

| Starting ingredient | Content (wt. %) |
|---|---|
| (Hydrophilic ingredient) | |
| MSE | 5.0 |
| Methyl parahydroxybenzoate | 0.1 |
| Refined water | 31.3 |
| (Lipophilic ingredient) | |
| White petrolatum | 40.0 |
| Cetanol | 18.0 |
| Sorbitan sesquioleate | 5.0 |
| Lauromacrogol | 0.5 |
| Butyl parahydroxybenzoate | 0.1 |

Comparative Example 11

A Japanese pharmacopoeial water-absorbing ointment was prepared in the same manner as Example 11, except that MSE was replaced by refined water.

EXAMPLE 12

To 50 g of MSE, a mixture of lactose, corn starch and a crystalline cellulose was added together with hydroxypropyl cellulose dissolved in 30 g of refined water, in the amounts shown in Table 12, and kneaded thoroughly. This kneaded mixture was passed through a 20 mesh sieve and granulated into granules followed by drying. The obtained granules were mixed with magnesium stearate and tableted into tablets of 200 mg/tablet. Thus, tablets containing 100 mg of active ingredients per tablet were obtained.

TABLE 12

| (Ingredient) | Content (g) |
|---|---|
| Lactose | 10 |
| Corn starch | 30 |
| Crystalline cellulose | 8 |
| Hydroxypropylcellulose | 1 |
| Magnesium stearate | 1 |

EXAMPLE 13

To 100 g of MSE, lactose, corn starch and a crystalline cellulose were added in the amounts shown in Table 13 and thoroughly mixed together. Capsules of the size No. 2 were loaded with 300 mg/capsule of the mixture. Thus, capsules containing 100 mg of active ingredients per capsule were obtained.

TABLE 13

| (Ingredient) | Content (g) |
|---|---|
| Lactose | 100 |
| Corn starch | 50 |
| Crystalline cellulose | 47 |
| Magnesium stearate | 3 |

EXAMPLE 14

To 100 g of MSE, lactose and corn starch were mixed thoroughly and a hydroxypropyl cellulose dissolved in 1,000 g of refined water was added in the amounts shown in Table 14, and kneaded thoroughly. This kneaded mixture was passed through a 20 mesh sieve and granulated. After drying, all the particle sizes were evened. Thus, granules containing 100 mg of MSE as an active ingredient per 1 g of granules were obtained.

TABLE 14

| (Ingredient) | Content (g) |
|---|---|
| Lactose | 470 |
| Corn starch | 400 |
| Hydroxypropylcellulose | 30 |

Comparative Experiment 1—Skin viscoelasticity test.

1) Test sample.

A pharmacopoeial water-absorbing ointment of Comparative Example 11 was blended with the compounding materials (Examples 1–10 and Comparative Examples 1~10) in the contents (wt.%) described in Tables 15~18 and creams as test samples were prepared. Additionally, an ointment without compounding these materials (Comparative Example 11) was used as a control.

2) Test method.

Male hairless rats of Wistar strain (6 weeks old; a weight of 110 g–130 g; 5 rats group) were hair-trimmed at their dorsal region. A test sample or the control ointment was applied everyday in an amount of 0.1 g/2 cm×2 cm area onto a right shoulder position. On the 45th day after the commencement of the test, a skin-viscoelasticity was measured with a vibration-type skin-viscoelastomer described in Japanese Patent Laid-open Application No. 59-120,130.

The mean viscoelasticity (S) of the group applied with the test sample and the mean viscoelasticity (C) of the group applied with the control ointment were found. Then, (S)/(C) was calculated to assess the viscoelasticity of the skin.

Additionally, as to the skin-viscoelasticity displayed on the above skin-viscoelastomer (in an arbitrary unit), the higher the value, the softer the skin is.

3) Test result.

The results are shown in Tables 15–18.

As is clear from those tables, all the test samples blended with MSE showed a promotion effect on skin-viscoelasticity.

Comparative Experiment 2—Human use test of hair growth promotion effect.

1) Test sample.

Examples 1–3 and Comparative Examples 1–3 (oily hair tonics) and Examples 4 and 5 and Comparative Examples 4–6 (hair creams) were used.

2) Test method.

Ten testees who were patients of androgenic alopecia had the hair of the scalp shaved into a round shape of a 1 cm diameter at two testing positions 5 cm above the both ears. The testing position on the left side was applied with about 3 ml of a test sample every morning and evening and compared with the untreated, right side position. On 28th day from the commencement of the test, 20 hairs each on both the testing positions were shaved off. The mean length (B) on the left side (applied with the test sample) and the mean length (A) on the right side (untreated) were found. The appraisal of the effect was shown by the mean (B)/(A) of 10 testees.

3) Test result.

The results are shown in Tables 15 and 16.

As is clear from the tables, all the test samples blended with MSE exhibited a growth promotion effect.

Comparative Experiment 3—Skin blood flow promotion test.

1) Test sample.

Examples 6–8 and Comparative Examples 7 and 8 (skin milks) and Examples 9 and 10 and Comparative Examples 9 and 10 (skin creams) were used.

2) Test method.

Three female rabbits of New Zealand white strain were hair-trimmed in both side abdominal regions. After fasting for 18 hours, 35 mg/kg of a pentobarbital sodium salt were intravenously injected to anesthetize. Immobilizing the back of the rabbit, a test sample or the control ointment was applied uniformly in an amount of 0.1 g onto two zones of 3 cm×2 cm in the side abdominal region, respectively. On these zones, a plate-type transducer was fixed with a cellophane tape, and with a crossed thermocouple type skin blood flow-meter (the trademark "UN METER™" Model 201, manufactured by Unique Medical Co., Japan), a skin blood flow (μV) was measured after 0.5, 1.0 and 2.0 hours from applying of the test samples.

Let the quantity of the blood flow when the test sample was applied be (A) and the quantity of the blood flow in the case of the control ointment be (B), and a blood flow ratio (A)/(B) was calculated. The mean value was found from all values obtained from every measurement at the above time with respect to three rabbits. Then, the maximum mean values of the blood flow ratio at respective times were further averaged and the thus averaged value represented a skin-blood flow increase ratio.

3) Test result.

The results are shown in Tables 17 and 18.

As is clear from the tables, the test samples blended with MSE exhibited a blood flow promotion effect.

TABLE 15

| Test Sample | Material blended in cream | Content (wt %) | Skin-visco-elasticity improvement | Human hair growth promotion |
|---|---|---|---|---|
| Example 1 | MSE | 0.1 | 1.11 | 1.18 |
| Example 2 | MSE | 0.5 | 1.30 | 1.25 |
| Example 3 | MSE | 4.0 | 1.42 | 1.34 |
| Comparative Example 1 | Red pepper tinctures | 0.1 | 0.95 | 1.01 |
| Comparative Example 2 | Japanese swertia extracts | 5.0 | 1.02 | 1.02 |
| Comparative Example 3 | Ethyl nicotinate | 0.1 | 1.01 | 1.00 |

TABLE 16

| Test Sample | Material blended in cream | Content (wt %) | Skin-visco-elasticity improvement | Human hair growth promotion |
|---|---|---|---|---|
| Example 4 | MSE | 0.2 | 1.15 | 1.15 |
| Example 5 | MSE | 3.0 | 1.36 | 1.38 |
| Comparative Example 4 | Red pepper tinctures | 0.1 | 1.00 | 1.01 |
| Comparative Example 5 | Panthenol | 2.0 | 0.98 | 1.02 |
| Comparative Example 6 | Biotin | 0.1 | 1.02 | 1.00 |

TABLE 17

| Test Sample | Material blended in cream | Content (wt %) | Skin-visco-elasticity improvement | Blood flow promotion |
|---|---|---|---|---|
| Example 6 | MSE | 0.1 | 1.12 | 1.20 |
| Example 7 | MSE | 1.0 | 1.32 | 1.23 |
| Example 8 | MSE | 4.0 | 1.43 | 1.50 |
| Comparative Example 7 | γ-oryzanol | 5.0 | 1.01 | 1.05 |
| Comparative Example 8 | Ethyl nicotinate | 0.1 | 1.02 | 1.01 |

TABLE 18

| Test Sample | Material blended in cream | Content (wt %) | Skin-visco-elasticity improvement | Blood flow promotion |
|---|---|---|---|---|
| Example 9 | MSE | 0.2 | 1.16 | 1.27 |
| Example 10 | MSE | 4.0 | 1.35 | 1.37 |
| Comparative Example 9 | Panthenol | 5.0 | 0.99 | 1.03 |
| Comparative Example 10 | Biotin | 0.1 | 1.01 | 1.05 |

Comparative Experiment 4—Effect on skin collagen.

Hairless rats having an insoluble skin collagen increased with aging were used for evaluation.

1) Test sample.

The ointment prepared in Example 11 (hereinafter abbreviated as "MSE ointment") and the pharmacopoeial ointment prepared in Comparative Example 11 (hereinafter abbreviated as "control ointment") were used.

2) Test method.

Fifteen male hairless rats of Wistar origin (6 weeks old; a weight of 110–130 g) were divided into 3 groups each consisting of 5 rats. Among them, one group was applied with the control ointment and another one group was applied with the MSE ointment, in an amount of 0.1 g onto the back right shoulder, once a day for continual 60 days. After 60 days, skins were cut off and subcutaneous fat was removed therefrom to provide specimens of skin of a 15 weeks old rat group applied with the control ointment (aged skins) and of a 15 weeks old rat group applied with the MSE ointment, respectively.

With respect to the remaining one group, skins were cut off from the back of the rats the instant that the test was commenced, to provide specimens of skin of an untreated, 6 weeks old rat group (young skins).

About 200 mg each of the specimens was added with 1 ml of physiological salt solution and subjected to 2 repetitive homogenizations at 28,000 rpm for 30 seconds with a homogenizer (PHYSCOTRON™). The blades of the homogenizer were washed with 1 ml of physiological saline and the saline was added to the above homogenized specimen. Further adding physiological saline, 2.4 ml of a suspension per 100 mg of the specimen of skin were provided.

The obtained suspension was shaken at 4° C. at 120 rpm for 24 hours and then centrifuged at 2,000 g for 10 minutes. Thus, a fraction solubilizable at 4° C. was obtained.

To the remaining precipitate, 10 ml of a Ringer's solution were added to homogenize. After shaking at 65° C. at 120 rpm for 45 minutes, centrifugation was conducted at 2,000 g for 10 minutes to provide a fraction solubilizable at 65° C.

To the remaining precipitate, 5 ml of refined water were added to homogenize and, after autoclaving at 120° C. for 60 minutes, centrifugation was conducted at 3,000 rpm for 10 minutes to provide a fraction solubilizable at 120° C.

The volume of these fractions was measured and each 1 ml of the fractions was added with 1 ml of a 12N-hydrochloric acid to completely hydrolyze at 110° C. for 24 hours. Then, hydrochloric acid was removed by centrifugal condensation and the resultant was redissolved with 1 ml of a 10 mM hydrochloric acid. With regard to the redissolved solution, the Hyp was quantified according to the aforementioned determination method of amino acids. The obtained value represented the quantity of the collagen.

3) Test result.

The results are shown in Table 19.

TABLE 19

| Treatment | Collagen (μmol Hyp/g of skin)[1) ] Solubilizing temperature 4° C. | 65° C. | 120° C. |
|---|---|---|---|
| 6 weeks old rats • Untreated | 42 ± 2* | 81 ± 6** | 11 ± 1** |
| 15 weeks old rats • Control ointment applied | 24 ± 5 | 157 ± 6 | 30 ± 2 |
| • MSE ointment applied | 44 ± 2* | 114 ± 3** | 26 ± 1** |

1) Mean value ± standard error (n = 5).
*Significantly different with a risk factor $p < 0.1$ as compared with the control ointment applied group (by Duncan's method).
**Significantly different with a risk factor $p < 0.01$ as compared with the control ointment applied group (by Duncan's method).

From the above table, it has been clarified that the MSE ointment restrains an increase of a constitutional proportion of a hard-extractable collagen (collagen with many crosslinkages) with aging and acts to maintain the constitutional proportion of the collagen on the level of 6 weeks old.

Comparative Experiment 5—Hair-growth practicality test.

1) Test sample.

The same as Comparative Experiment 2.

2) Test method.

Onto the scalps of 20 testees who were patients of androgenic alopecia, a test sample was applied every morning and evening for continual 6 months. Then, the effects were appraised. The hair growth stimulative effect, hair falling-off preventive effect, dandruff preventive effect were shown by the number of the testees answered "downs were thickened or increased in number", "hair falling-off was lessened" and "dandruff was decreased", respectively.

3) Test result.

The results are shown in Tables 20 and 21.

TABLE 20

| Test Sample | Material blended in test cream | Content (wt %) | Practicality test (No. of persons) Hair growth | Prevention of hair falling-off | Prevention of dandruff |
|---|---|---|---|---|---|
| Example 1 | MSE | 0.1 | 15 | 15 | 10 |
| Example 2 | MSE | 0.5 | 16 | 17 | 12 |
| Example 3 | MSE | 4.0 | 18 | 17 | 14 |
| Comparative Example 1 | Red pepper tinctures | 0.1 | 5 | 7 | 4 |
| Comparative Example 2 | Japanese swertia extracts | 5.0 | 4 | 6 | 6 |
| Comparative Example 3 | Ethyl nicotinate | 0.1 | 5 | 6 | 5 |

TABLE 21

| Test Sample | Material blended in test cream | Content (wt %) | Practicality test (No. of persons) Hair growth | Prevention of hair falling-off | Prevention of dandruff |
|---|---|---|---|---|---|
| Example 4 | MSE | 0.2 | 16 | 15 | 11 |
| Example 5 | MSE | 3.0 | 18 | 18 | 13 |
| Comparative Example 4 | Red pepper tinctures | 0.1 | 4 | 7 | 4 |
| Comparative Example 5 | Panthenol | 2.0 | 5 | 5 | 6 |
| Comparative Example 6 | Biotin | 0.1 | 4 | 5 | 5 |

From these tables, the effect of MSE was clearly recognized also in the practicality test.

Comparative Experiment 6—Practicality-to-skin test.

1) Test sample.

The same as Comparative Experiment 3.

2) Test method.

Twenty female testees (35–55 years of age) who complained of rough skin, fine wrinkles, dry skin and the like of their face, were made to use a test sample every morning and evening continuously for 3 months. Then, the testees appraised the effect with respect to improvements of skin in softness, elasticity and wrinkles. The effects of the above items were shown by the number of the testees that answered "the softness of the skin has been improved", "the elasticity of the skin has been improved" and "the wrinkles of the skin have been ameliorated", respectively.

3) Test result.

The results are shown in Tables 22 and 23.

TABLE 22

| Test Sample | Material blended in test cream | Content (wt %) | Practicality test (No. of persons) Soft-ness | Elas-ticity | Wrinkle amelioration |
|---|---|---|---|---|---|
| Example 6 | MSE | 0.1 | 14 | 16 | 13 |
| Example 7 | MSE | 1.0 | 17 | 18 | 14 |
| Example 8 | MSE | 4.0 | 16 | 18 | 15 |
| Comparative Example 7 | γ-oryzanol | 5.0 | 6 | 8 | 8 |
| Comparative Example 8 | Ethyl nicotinate | 0.1 | 7 | 9 | 7 |

TABLE 23

| Test Sample | Material blended in test cream | Content (wt %) | Practicality test (No. of persons) Soft-ness | Elas-ticity | Wrinkle amelioration |
|---|---|---|---|---|---|
| Example 9 | MSE | 0.1 | 14 | 16 | 12 |
| Example 10 | MSE | 4.0 | 19 | 19 | 15 |
| Comparative Example 9 | Panthenol | 5.0 | 7 | 6 | 7 |
| Comparative Example 10 | Biotin | 0.1 | 6 | 8 | 7 |

From these tables, the effect of MSE was clearly recognized also in the practicality test. Industrial applicability When MSE according to the present invention is added to a culture system of a human fibrosarcoma cell strain, the production of the procollagenase is promoted.

In the test using animals, it has been confirmed that MSE is effective for medical treatments of diseases accompanied with an abnormal accumulation of collagen, for example, hepatic fibrosis.

MSE according to the present invention is a safe compound free from toxicity and skin irritation.

Further, it has been confirmed that a skin collagen composition to be otherwise insolubilized with aging, is kept young.

Moreover, its effects have been recognized in the practicality tests as hair growth stimulants and skin aging inhibitors.

From the above, it is clearly recognized that MSE according to the present invention is efficacious, as a collagen metabolism ameliorant as well as a hair growth stimulant and a skin aging inhibitor, against collagen hypometabolism caused by aging or diseases accompanied with an abnormal accumulation of collagen.

We claim:

1. A method for ameliorating collagen hypometabolism in skin tissue, said method comprising the step of administering N-methyl-L-serine in a dosage between 0.1 and 1,000 mg to a human patient having the skin tissue.

2. A hair cosmetic comprising a dispersion made up of about 5–50% by weight of a lipophilic ingredient and about 50–95% by weight of a hydrophilic ingredient containing N-methyl-L-serine in an amount of 0.001–10% by weight based on the total weight of the hair cosmetic.

3. A dermal cosmetic comprising an emulsion made up of about 25–65% by weight of a lipophilic ingredient and about 35–75% by weight of a hydrophilic ingredient containing N-methyl-L-serine in an amount of 0.001–10% by weight based on the total weight of the dermal cosmetic.

4. A method of stimulating hair growth in skin tissue, said method comprising the step of administering N-methyl-L-serine in a dosage between 0.1 and 1,000 mg to a human patient having the skin tissue.

5. A method of promoting viscoelasticity in skin tissue, said method comprising the step of administering N-methyl-L-serine in a dosage between 0.1 and 1,000 mg to a human patient having the skin tissue.

* * * * *